US007531005B1

(12) United States Patent
Healy et al.

(10) Patent No.: US 7,531,005 B1
(45) Date of Patent: May 12, 2009

(54) BIODEGRADABLE COMPOSITE MATERIAL FOR TISSUE REPAIR

(75) Inventors: David Michael Healy, Ayr (GB); Thomas Gilchrist, Ayr (GB)

(73) Assignee: Tyco Healthcare Group LP, Mansfield, MA (US)

( * ) Notice: Subject to any disclaimer, the term of this patent is extended or adjusted under 35 U.S.C. 154(b) by 577 days.

(21) Appl. No.: 09/913,139

(22) PCT Filed: Feb. 11, 2000

(86) PCT No.: PCT/GB00/00475

§ 371 (c)(1), (2), (4) Date: Aug. 10, 2001

(87) PCT Pub. No.: WO00/47245

PCT Pub. Date: Aug. 17, 2000

(30) Foreign Application Priority Data

Feb. 11, 1999  (GB) .................................. 9902976.1

(51) Int. Cl.
*A61F 2/28* (2006.01)
*C03C 3/19* (2006.01)

(52) U.S. Cl. ..................................... 623/23.61; 501/47

(58) Field of Classification Search ............. 623/16.11, 623/23.51, 23.52, 23.53, 23.54, 23.55, 23.56, 623/23.57, 23.58, 23.59, 23.61; 148/669, 148/421; 420/417, 421; 428/357, 382, 397; 424/443, 445, 444, 446, 447, 449; 501/35, 501/45, 47; 242/602; 106/600
See application file for complete search history.

(56) References Cited

U.S. PATENT DOCUMENTS

| | | | | |
|---|---|---|---|---|
| 4,517,006 A | * | 5/1985 | Drake et al. ................. | 71/64.11 |
| 4,604,097 A | * | 8/1986 | Graves et al. ................ | 424/422 |
| 4,655,777 A | * | 4/1987 | Dunn et al. .................. | 424/423 |
| 5,222,987 A | * | 6/1993 | Jones ......................... | 623/66.1 |
| 5,439,985 A | * | 8/1995 | Gross et al. ................. | 525/411 |
| 5,604,270 A | * | 2/1997 | Klett et al. .................. | 523/421 |
| 5,645,934 A | * | 7/1997 | Marcolongo et al. ......... | 428/357 |
| 5,760,118 A | * | 6/1998 | Sinclair et al. .............. | 524/306 |
| 6,210,703 B1 | * | 4/2001 | Novich ........................ | 424/443 |
| 6,309,422 B1 | * | 10/2001 | Farrington et al. ........ | 623/23.51 |

FOREIGN PATENT DOCUMENTS

| | | | | |
|---|---|---|---|---|
| DE | 195 08 647 A1 | | 1/1996 | |
| EP | 0 146 398 A2 | | 6/1985 | |
| EP | 0146398 | * | 6/1985 | .............. 623/23.61 |
| EP | 0494358 | * | 7/1992 | ................. 523/421 |
| GB | 2 169 914 A | | 7/1986 | |
| JP | 10298108 | | 11/1998 | |
| WO | WO 90/04982 | * | 5/1990 | |
| WO | WO 97/33632 A2 | | 9/1997 | |
| WO | WO 98/44965 | * | 10/1998 | .............. 623/23.61 |
| WO | WO 98/44965 A1 | | 10/1998 | |
| WO | WO 98/54104 | | 12/1998 | |
| WO | WO 99/11296 | * | 3/1999 | .............. 623/23.61 |
| WO | WO 99/11296 A2 | | 3/1999 | |

OTHER PUBLICATIONS

Corden, T.J., et al., *Composites: Part A*, 30:737-746 (1999).

* cited by examiner

*Primary Examiner*—Pedro Philogene
(74) *Attorney, Agent, or Firm*—Douglas E. Denninger, Esq.

(57) ABSTRACT

There is described a biodegradable composite material for tissue repair comprising a water-soluble glass, preferably as glass fibers and/or particles in the form of a matrix, impregnated with a biodegradable polymer. An especially preferred polymer is poly ε-caprolactone. The biodegradable composite is particularly useful for the repair of nerve and/or bone tissue, especially the bones of the skull. A method of producing the composite material is also described.

20 Claims, No Drawings

BIODEGRADABLE COMPOSITE MATERIAL FOR TISSUE REPAIR

The present invention relates to a composite material which is especially useful in bone repair.

Most commonly defects to bone arise from injury, but may also be due to congenital abnormalities, to acquired deformity or to ablation of tumours. Without adequate repair, bone defects can significantly affect function of the associated limb, and frequently the mobility of the patient is impaired. Where the bone defect is present in the skull, there may be cosmetic considerations and without adequate repair the appearance of the patient may be adversely affected.

Repair and reconstruction of defective bone currently involves either the use of auto-graft tissue (ie where bone is removed from another part of the patient's body and used for repair) or the use of bio-compatible materials. Allograft bone transplants (ie using donated bone material) are still the main source of material for bone repair, despite the risk of disease transmission, notably HIV or CJD, due to contaminated sources. Both of the current approaches also suffer other disadvantages: the need to obtain bone from the patient for use in the auto-graft requires further invasive procedure(s) and a second wound site in the patient; and the bio-compatible materials currently available are not suitable for all types of bone repair and are particularly inadequate for repairing defects of the skull.

The present invention provides a biodegradable composite material suitable for implantation in a patient's body, said composite material comprising water-soluble glass and a biodegradable polymer.

The water-soluble glass material may be in the form of fibres, particles or mixtures thereof. As used herein the term "glass fibres" refers to glass in both wool and mono-filament form. The length of the fibres is not critical and would normally be chosen to suit the size of composite required.

Examples of suitable water-soluble glass fibres include the fibres described in WO-A-98/54104, WO-A-99/62834 and WO-A-99/62835 (all in the name of Giltech Limited), the content of each of these publications being incorporated herein by reference.

The biodegradable polymer may be any suitable biocompatible polymer or mixtures of such polymers. Preferably the polymer exhibits some pliability or plasticity. Examples include (but are not limited to) polyvinyl alcohols, polysaccharides (for example alginates and chitosan), polyglycolic acid, polylactic acid, polyglycolactide, polyhydroxybutyrate, polyhydroxyvaleriate, polycaprolactones (for example poly ε-caprolactone), polycaprolactam and starches (especially "thermoplastic" starches such as hydroxypropylated starches, or potato, maize or rice starch treated by high pressure or humidity). Copolymers of these polymers may also be used (for example polyglycolide (or polyglycolic acid)/polycaprolactone co-polymer or a polyglycolic acid/polycaprolactam co-polymer).

A preferred biodegradable polymer is poly (ε-caprolactone), or or any other slowly degrading polymer material.

In one embodiment, the water-soluble glass material will degrade more slowly (and usually at a significantly slower rate) than the biodegradable polymer. Alternatively, the biodegradable polymer will degrade more slowly than the water-soluble glass material.

Advantageously the glass material, in addition to contributing to the strength of the composite material, will provide a suitable environment for initiation of bone repair. Desirably therefore osteoblasts are able to penetrate the biodegradable polymer in order to attach to the glass material and commence bone formation. Generally the size of the glass material will be selected to degrade in a time-scale comparable to bone repair.

The polymer provides a sponge-like environment around the water-soluble glass, and becomes wetted by body fluids when the composite material is placed in the body. Where water-soluble glass particles or fibres are present in the composite, slight dissolution of polymer occurs around the sites where the glass is present and may cause a general loosening of the composite. The degree of loosening may be beneficial in some embodiments since the areas created are available for tissue ingrowth. Loss of mechanical strength in the composite material may be countered by including randomly orientated fibres and/or the release of zinc ions from the glass, which would promote cross-linking and repolymerisation of the polymer (especially poly ε-caprolactone) around the glass.

A further advantage of the composite described is that it is mouldable, and it may be contoured to fit the implant site closely.

The composite material may comprise a matrix of water-soluble glass material, the matrix being impregnated with the biodegradable polymer. Optionally the glass material (fibres and/or particles) is arranged to provide adequate strength in the load-bearing dimensions of the composite.

In a further aspect the present invention provides a method of repairing an area of defective tissue (for example nerve or bone) in a patient, said method comprising implanting a composite material as described above into said patient in sufficient quantity to cover and/or fill said area. Optionally said composite material is attached to healthy tissue using conventional (preferably biodegradable) means. Mention may be of sutures and biodegradable glue in this respect.

The biodegradable composite of the present invention may be used to form pins, plates, nuts or bolts to hold shattered bone pieces together, or may be formed into flexible sheet form to wrap around a defective tissue.

In a further aspect, the present invention provides a method of producing a composite material suitable for tissue repair, said method comprising:

a) providing water-soluble glass fibres and/or glass particles;
b) optionally arranging said fibres and/or particles into a pre-selected order;
c) covering said fibres and/or particles with a biodegradable polymer and if required allowing said polymer to cure.

In one embodiment the composite material may be formed using liquid moulding techniques. For example the required array of glass fibres and/or particles may be positioned in a closed mould cavity into which the polymer is then introduced. A rigid composite material is formed once the polymer has cured. Optionally introduction of the polymer into the mould may be vacuum assisted.

Where poly(ε-caprolactone) is used as the polymer, conducting the polymerisation reaction within the mould cavity itself may be desirable since introduction of this polymer into the mould is difficult due to the high viscosity of poly(ε-caprolactone). A ring-opening polymerisation of caprolactone using 1,4-butanediol catalyzed with diethylzinc may be suitable for such in situ polymerisation.

Alternatively, a suitable composite material may be produced by forming glass fibre into a glass fibre fabric which can then be simply dipped into the plastic polymer. Alternatively, the polymer may be sprayed onto the fibre. In addition to the techniques of thermoforming and weaving, the glass fibres could also be spun into a yarn, the fibres or yarn being optionally knitted, braided or crocheted. Likewise where glass wool is used, the wool may be shaped as required and either dipped into the plastic polymer or placed into a closed mould cavity for liquid moulding as described above.

In a further embodiment glass particles are used together with short lengths of glass fibres.

In a yet further aspect, the present invention provides the use of a composite material as described above for repairing damaged or defective tissue (especially bone or nerve tissue) in a body.

Desirably the composite material is sterilised prior to implantation in the body, for example by irradiation.

Phosphorus pentoxide ($P_2O_5$) is preferably used as the glass former.

Generally the mole percentage of phosphorous pentoxide in the glass composition is less than 85%, preferably less than 60% and especially between 30-60%.

Alkali metals, alkaline earth metals and lanthanoid oxides or carbonates are preferably used as glass modifiers.

Generally, the mole percentage of alkali metals, alkaline earth metals and lanthanoid oxides or carbonates is less than 60%, preferably between 40-60%.

Boron containing compounds (eg $B_2O_3$) are preferably used as glass additives.

Generally, the mole percentage of boron containing compounds is less than 15% or less, preferably less than 10%, and usually around 5% or less.

Other compounds may also be added to the glass to modify its properties, for example $SiO_2$, $Al_2O_3$, $SO_3$ or transition metal compounds (eg. first row transition metal compounds). Generally, the glass will release ionic species upon dissolution, the exact ionic species released depending upon the compounds added to the glass. Glasses which release aluminum ions, sulphate ions or fluorine ions may be desirable in some circumstances.

Typically the soluble glasses used in this invention comprise phosphorus pentoxide ($P_2O_5$) as the principal glass-fromer, together with any one or more glass-modifying non-toxic materials such as sodium oxide ($Na_2O$), potassium oxide ($K_2O$), magnesium oxide (MgO), zinc oxide (ZnO) and calcium oxide (CaO). The rate at which the glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. remaining from substantially zero to 25 mg/cm²/hour or more can be designed. However, the most desirable dissolution rate R of the glass is between 0.01 and 2.0 mg/cm²/hour.

The water-soluble glass is preferably a phosphate glass, and may comprise a source of silver ions which may advantageously be introduced during manufacture as silver orthophosphate ($Ag_3PO_4$). Other metals may alternatively or additionally be present and mention may be made of Cu, Mg, Zn, Ce, Mn, Bi, Se, Cs. Preferred metals include Ag, Cu, Zn and Mg. The glass preferably enables controlled release of metal and other constituents in the glass and the content of these additives can vary in accordance with conditions of use and desired rates of release, the content of metal generally being up to 5 mole %. While we are following convention in describing the composition of the glass in terms of the mole % of oxides, of halides and of sulphate ions, this is not intended to imply that such chemical species are present in the glass nor that they are used for the batch for the preparation of the glass.

The optimum rate of release of metal ions into an aqueous environment may be selected by circumstances and particularly by the specific function of the released metal. The invention provides a means of delivering metal ions to an aqueous medium at a rate which will maintain a concentration of metal ions in said aqueous medium of not less than 0.01 parts per million and not greater than 10 parts per million. In some cases, the required rate of release may be such that all of the metal added to the system is released in a short period of hours or days and in other applications it may be that the total metal be released slowly at a substantially uniform rate over a period extending to months or even years. In particular cases there may be additional requirements, for example it may be desirable that no residue remains after the source of the metal ions is exhausted or, in other cases, where the metal is made available it will be desirable that any materials, other than the metal itself, which are simultaneously released should be physiologically harmless. In yet other cases, it may be necessary to ensure that the pH of the resulting solution does not fall outside defined limits.

Generally, the mole percentage of these additives in the glass is less than 25%, preferably less than 10%.

Embodiments of the invention will be described with reference to the following non-limiting examples.

EXAMPLE 1

Method of Forming a Glass Fibre

The glass-forming composition is initially heated to a melting temperature of 500°-1200° C., preferably 750°-1050° C. The temperature is then slowly lowered to the working temperature at which fibre formation occurs.

Generally, the working temperature of the glass will be at least 200° C. lower than the temperature at which the glass is initially heated. Suitable working temperatures may fall within the following ranges 400°-500° C., 500°-900° C. (preferably 550°-700° C., more preferably 550°-650° C., especially 600°-650° C.) and 800-1000° C. The working temperature selected will depend upon the glass composition, but an approximate indication of a suitable working temperature can be established as hereinafter described. Depending upon the glass composition used, the working temperature may be a range of suitable temperatures. The range of working temperatures may be narrow, for example of only 10° C., so that fibre formation may occur only between the temperature of N° C. to (N+10)° C. Other glass compositions may have a wider temperature range for the working temperature in which glass formation is possible.

Alternatively, the working temperature of the glass may be defined as 50-300° C. above the Tg of the glass.

In order to obtain an approximate indication of the working temperature for any particular glass composition, the glass composition should be slowly heated to its melting point. As soon as the glass is molten, frequent attempts to pull the composition upwardly to form a fibre should be made, with the temperature of the composition being very gradually increased between attempts. The temperature range of the composition during which fibre formation is possible should be noted and used as a preliminary working temperature in the process of the invention.

It will be clear to those skilled in the art that the pulling speed at which the fibre is drawn off can affect the choice of working temperature and the diameter of the fibre required. Where a fibre of relatively large diameter is required, the fibre tends to be pulled more slowly and the working temperature may need to be decreased slightly. Where a fibre of relatively small diameter is required (eg a glass wool), the fibres may be drawn at the much higher pulling speed and the working temperature may need to be increased (thus lowering the viscosity of the composition to accommodate the increased pulling speed). Selection of the exact working temperature in respect of any particular fibre size and composition will be a simple matter of routine evaluation of optimal process conditions.

With reference to the "working temperature" of the glass, the skilled person will appreciate that the furnace temperature may differ considerably from the temperature of the glass itself and indeed there may be a significant temperature gradient in the glass. Ideally the "working temperature" will be the temperature of the glass as fibre formation (ie. pulling) takes place. In many compositions however, it may not be practical to measure the temperature at the surface of the glass where pulling occurs by insertion of a temperature probe as the introduction of the probe may precipitate crystallization of the glass. One alternative is to place a temperature probe into the bushing and to monitor the bushing temperature which will be a good indicator of the glass temperature at the moment of fibre formation. Alternatively an Infra Red pyrometer may be focused onto the appropriate area of the glass and used to monitor the temperature.

The glass to be formed into fibres will generally be heated until molten, optionally clarified, and then cooled slowly and controllably until the appropriate working temperature is reached and fibre formation can commence. The initial heating of the glass above its melting point and the subsequent fibre formation may be carried out in a single vessel or, alternatively, the molten glass may be transferred to a vessel designed specifically for fibre formation. One way of holding the molten glass in a vessel having a bushing within its lower surface until the temperature drops to the required working temperature is to coat or fill the holes of the bushing with a material that gradually melts over the period of time taken for the glass to reach the temperature required.

The most important aspect of the method is the manner in which the working temperature is reached. We have found that the molten glass, which may preferably be heated significantly above its melting point, should be allowed to cool in a highly controlled manner, the temperature being only gradually reduced until the working temperature is reached. A stirrer may be present to ensure that the temperature of the whole of the molten glass is kept as uniform as possible.

The glass is cooled to a temperature at which the glass will not crystallise for at least the period of time needed to convert the melt to fibre. This temperature is termed herein as a "holding temperature". The rate of cooling from this holding temperature is determined by the rate at which the melt is consumed at the bushing and the difference in temperature between the bushing temperature (the working temperature) and the melt holding temperature.

Due to low viscosity and narrow temperature band for many of these compositions, control of the balance between melt temperature, bushing temperature and glass throughput rate is critical.

Examples 2 to 16 detail suitable compositions which can be formed into fibres using the method of Example 1. Alternatively, these glasses can be cast in a conventional way and used to form particles, powder or granules.

|  | Component | Mole % |
|---|---|---|
| Glass Composition | $Na_2O$ | 31.05 |
|  | CaO | 16.00 |
|  | $Ag_2O$ | 3.88 |
|  | $P_2O_5$ | 46.08 |
|  | $Na_2PO_3F$ | 0.97 |
|  | $2Al_2O_3 \cdot B_2O_3$ | 2.00 |

100 grams of the sample was heated to 900° C. before being cooled and pulled at 650° C., at 25 km/hr. Overall the fibre was good; one example was 10 km in length and 11 grams in weight, although there was some crystallisation at the pulling temperature.

EXAMPLE 3

|  | Component | Mole % |
|---|---|---|
| Glass Composition | $Na_2O$ | 29.51 |
|  | CaO | 15.21 |
|  | $Ag_2O$ | 3.68 |
|  | $P_2O_5$ | 43.80 |
|  | $2Al_2O_3 \cdot B_2O_3$ | 1.90 |
|  | $Na_2PO_3F$ | 1.90 |
|  | $Na_2B_4O_7 \cdot 10H_2O$ | 1.00 |
|  | $Na_2PO_4$ | 3.00 |

74 grams of the sample was heated to 1000° C. before being cooled and pulled at 635° C. at 25 km/hr. The fibre produced was ultrafine; one sample was 18 km in length and 59 grams in weight. The sample was sprayed with WD40 to prevent water absorption and to aid lubricity. There was some debris at the bottom of the crucible, but this was found to be just iron deposits from the brushing rod.

EXAMPLE 4

|  | Component | Mole % |
|---|---|---|
| Glass Composition | $Na_2O$ | 34.20 |
|  | CaO | 16.15 |
|  | $P_2O_5$ | 44.65 |
|  | $Na_2SO_4$ | 5.00 |

200 grams of the sample was heated to 1050° C. before being cooled and pulled at 635° C. at 25 km/hr. The fibre was good although there was some crystallisation at the pulling temperature.

EXAMPLE 5

|  | Component | Mole % |
|---|---|---|
| Glass Composition | $Na_2O$ | 32.40 |
|  | CaO | 15.30 |
|  | $P_2O_5$ | 42.30 |
|  | $2Al_2O_3 \cdot B_2O_3$ | 3.00 |
|  | $Na_2PO_3F$ | 1.00 |
|  | $Na_2SO_4$ | 6.00 |

117 grams of the sample was heated to 950° C. before being cooled and pulled at 635° C., at 40 km/hr. The fibre produced was good and there were no crystallisation problems even though the surface temperature of the fibre dropped to 510° C. in the pulling process.

EXAMPLE 6

|  | Component | Mole % |
|---|---|---|
| Glass Composition | Na$_2$O | 31.71 |
|  | CaO | 14.73 |
|  | P$_2$O$_5$ | 36.33 |
|  | B$_2$O$_3$ | 4.78 |
|  | SO$_3$ | 9.40 |
|  | Na$_2$PO$_3$F | 3.00 |

99 grams of the sample was heated to 800° C. before being cooled to 650° C. and pulled at 40 km/hr. The fibre produced was very fine but difficult to pull and quite fragile at speed.

EXAMPLE 7

|  | Component | Mole % |
|---|---|---|
| Glass Composition | Na$_2$O | 30.77 |
|  | CaO | 14.28 |
|  | P$_2$O$_5$ | 35.28 |
|  | B$_2$O$_3$ | 4.64 |
|  | SO$_3$ | 9.12 |
|  | FePO$_4$ | 2.41 |
|  | Na$_2$PO$_3$F | 0.20 |
|  | Na$_2$PO$_3$F | 0.20 |
|  | MnHPO$_4$ | 2.06 |

200 grams of the sample was heated to 850° C. before being cooled to 545° C. and pulled at 40 km/hr. The fibre produced was strong and thin; there was not a problem of crystallisation, in fact the glass can be stored at 550° C. for 72 hours without the onset of crystallisation.

EXAMPLE 8

Below is an example of a wool formulation and running conditions to illustrate the differences with the monofilament examples given above.

| A typical wool formulation is | |
|---|---|
| Na$_2$O | 26.31 |
| CaO | 17.78 |
| P$_2$O$_5$ | 47.04 |
| B$_2$O$_3$ | 5.94 |
| MnO | 1.55 |
| Fe$_2$O$_3$ | 0.97 |
| NaF | 0.41 |

Solution rate, not annealed=0.0278 mg.cm$^{-2}$hr$^{-1}$
Melted and refined at 1000° C.
Cooled and held at 725° C.
Bushing temperature maintained at 365° C.
Thick fibres approx 1.2 mm diameter drawn through pinch rollers at 2.5 M.mm$^{-1}$ from a bushing with 6×6.5 mm diameter holes. Fibres jet attenuated to produce a fine wool 5-15 μm diameter. The wool was sprayed with silicone oil finish during the attenuation process and collected on a stainless steel mesh conveyor.

Typically, attenuated wools will have diameters of 5 to 20 μm. Monofilament fibres will mostly be 20 to 50 μm diameter.

EXAMPLE 9

| Na$_2$O | 31.19 mole % |
|---|---|
| K$_2$O | 9.63 mole % |
| Ag$_2$O | 2.9 mole % |
| B$_2$O$_3$ | 2.74 mole % |
| 2NaF | 0.66 mole % |
| P$_2$O$_5$ | 52.88 mole % |

Furnace at 710° C.-800° C.
Bushing at 450° C.-460° C.
4.5 mm bushing holes.
50 km per hour pull rate.
Good fibres.
Solution rate=1.68 not annealed 2.28 annealed.

EXAMPLE 10

| Na$_2$O | 32 mole % |
|---|---|
| K$_2$O | 10 mole % |
| Ag$_2$O | 3 mole % |
| P$_2$O$_5$ | 55 mole % |

Furnace at 850° C.
Bushing at 530° C.
5 mm bushing holes.
55 kmph.
Good strong fibres.

EXAMPLE 11

| Na$_2$O | 32 mole % |
|---|---|
| K$_2$O | 10 mole % |
| (MgO | 4 mole %) - added as an anti-microbial |
| B$_2$O$_3$ | 5 mole % |
| Ag$_2$O | 3 mole % |
| P$_2$O$_5$ | 46 mole % |

Furnace temperature 650° C.-730° C.
Bushing temperature 410° C.-420° C.
Bushing 5.5 mm diameter.
Speed up to 100 kmph.
Solution rate 0.7 annealed 1.0 non annealed (mg.cm$^{-3}$.hr$^{-1}$).
Very good strong reliable fibre. Very stable.

EXAMPLE 12

| Na$_2$O | 36.68 mole % |
|---|---|
| K$_2$O | 8.63 mole % |
| P$_2$O$_5$ | 45.09 mole % |
| B$_2$O$_3$ | 5.29 mole % |
| Ag$_2$O | 2.59 mole % |
| (CaO | 1.73 mole % to attenuate solution rate! |

Furnace temperature 550° C.
Bushing 62×5.0 mm holes.
Bushing temperature 400° C.
Speed 80 kmph.
Very good fibres.
Solution rate 3.11 annealed, 3.8 non annealed (mg.cm$^-$$_2$.hr$^{-1}$).

The fibres show excellent tensile strength, flexibility and shock resistance.

The fibres are especially suitable for industrial and plastics reinforcement controlled release (anti-microbial, anti-corrosion etc) and rapidly biodegradable applications.

EXAMPLE 13

| | |
|---|---|
| CaO | 30 mole % |
| MgO | 20 mole % |
| P$_2$O$_5$ | 50 mole % |

Furnace at 1050° C.
Bushing 5.5 mm holes.
Bushing temperature 700° C.-720° C.
Speed up to 80 kmph.
Solution rate TBA.
Very strong fibre.

EXAMPLE 14

| | | |
|---|---|---|
| (K$_2$O | 5 mole %) | Trace to alter dissolution rate |
| CaO | 25 mole % | |
| Mg$_2$O | 20 mole % | |
| P$_2$O$_5$ | 50 mole % | |

Furnace 1000° C.
Bushing 5.5 mm.
Bushing temperature 560° C.-620° C.
Speed up to 70 kmph.
Solution rate TBA.
Very strong fibre.
Anti-microbial.

EXAMPLE 15

| | |
|---|---|
| CaO | 28.5 mole % |
| MgO | 18.5 mole % |
| Ag$_2$O | 3 mole % |
| P$_2$O$_5$ | 50 mole % |

Furnace temperature 1050° C.-1150° C.
Bushing 4×5.5 mm.
Bushing temperature 700° C.
Speed 50 kmph.
Solution rate TBA.
Very good, strong fibre.
Anti-microbial.

EXAMPLE 16

| | |
|---|---|
| CaO | 30 mole % |
| MgO | 20 mole % |
| P$_2$O$_5$ | 50 mole % |

As Example 15 (without silver)

The fibres show excellent tensile strength, flexibility and shock resistance. These fibres are suitable for applications requiring slower release and greater tensile strength plus biodegradability. The fibres are suitable for orthpaedic implants and tissue engineering applications.

EXAMPLE 17

Producing a composite comprising soluble glass powder or granules.

Glass powder or granules can be added to the polymer to reinforce, stiffen or bulk the composite. The glass (for example based on the glasses of any of Examples 1 to 16) can be used to release, for example, antimicrobials or trace elements. The glass, whose solution rate can be varied as required, reduces the volume of polymer to be degraded when used as a bulking agent.

The powder or granules/polymer composition can be made in various ways, as follows:

1. Mixing the glass with solvent dissolved polymer, e.g. polycaprolactone can be dissolved in chloroform. Glass is added to the liquid and mixed. The solvent is evaporated to leave the composite.
2. The glass can be mixed into melted polymer.
3. The glass can be added to polymer masterbatch which can then be used in extrusion or co-extrusion processes.

EXAMPLE 18

Producing a composite comprising soluble glass fibre.

The addition of biodegradable glass fibre (as described in any of Examples 1 to 16 ) for reinforcement, bulking or controlled release in the polymer may be achieved by various methods, as follows:

1. Fibre can be passed through a bath of polymer dissolved in solvent. The polymer solution can also be applied by passing the fibre over a rotating or counter-rotating transfer roller.
2. Solvent dissolved polymer can be sprayed directly onto fibre as it is collected onto a drum or atomised into the jet attenuation venturi to produce coated wool.
3. Continuous fibre can be fed through a bath of melted polymer.
4. Fibre can be mixed into melted polymer or knitted or pre-formed into shapes to be layered into melted polymer. It may be possible to make sheets of polymer/fibre "sandwich" which can be thermally formed in a press.

The invention claimed is:

1. A biodegradable composite material suitable for implantation into a patient's body, said composite material comprising water soluble glass fibers and a biodegradable polymer, wherein said water soluble glass fibers comprise from 30 mole % to less than 85 mole % of phosphorous pentoxide, and wherein said water soluble glass fibers comprise a mixture of water soluble glass fibers and water soluble glass particles.

2. The composite material as claimed in claim 1, wherein said biodegradable polymer is a polyvinyl alcohol, polysaccharide, polyglycolic acid, polylactic acid, polyhydroxybutyrate, polyhydroxyvaleriate, polycaprolactone, polycaprolactam or a starch.

3. The composite material as claimed in claim 2, wherein said biodegradable polymer is poly $\epsilon$-caprolactone.

4. The composite material as claimed in claim 1, which comprises a matrix of a mixture of water soluble glass fibers and water soluble glass particles, impregnated with said biodegradable polymer.

5. The composite material as claimed in claim 2, wherein said biodegradable polymer is a starch.

6. The composite material as claimed in claim 5, wherein the starch is selected from the group consisting of a thermoplastic starch, a hydroxypropylated starch, a potato starch, a maize starch, and a rice starch.

7. The biodegradable composite material as claimed in claim 1, further comprising an antimicrobial material.

8. The biodegradable composite material as claimed in claim 1, further comprising a metal selected from the group consisting of copper magnesium, zinc, cerium, manganese, bismuth, selenium, cesium, and mixtures thereof.

9. The biodegradable composite material as claimed in claim 1, further comprising a source of silver ions.

10. The biodegradable composite material as claimed in claim 9, wherein the biodegradable polymer is a starch.

11. The biodegradable composite material as claimed in claim 1, wherein the water soluble glass fibers further comprise a metal selected from the group consisting of silver, copper, magnesium, zinc, cerium, manganese, bismuth, selenium, cesium, and mixtures thereof.

12. The biodegradable composite material as claimed in claim 11, wherein the biodegradable polymer is a starch.

13. A method of producing a composite material suitable for tissue repair, said method comprising:

a) providing a mixture of water soluble glass fibers and water soluble glass particles comprising from 30 mole % to less than 85 mole % of phosphorous pentoxide;

b) optionally arranging said mixture into a pre-selected order; and c) covering said mixture with a biodegradable polymer and if required allowing said polymer to cure.

14. The method as claimed in claim 13, wherein said biodegradable polymer is poly $\epsilon$-caprolactone and wherein polymerisation occurs within a mould.

15. A method of repairing an area of defective tissue in a patient, said method comprising inserting a biodegradable composite material suitable for, implantation into a patient's body, said composite material comprising water soluble glass fibers and a biodegradable polymer into said patient in a quantity sufficient to cover and/or fill said area, wherein said water soluble glass fibers comprise from 30 mole % to less than 85 mole % of phosphorous pentoxide, and wherein said composite material comprises a mixture of water soluble glass fibers and water soluble glass particles.

16. The method as claimed in claim 15, wherein the area of defective tissue is an area of nerve or bone in need of repair.

17. The method as claimed in claim 15, wherein said composite material is attached to healthy tissue by suture and/or by biodegradable adhesive.

18. The method of claim 9, wherein said biodegradable polymer is a polyvinyl alcohol, polysaccharide, polyglycolic acid, polylactic acid, polyhydroxybutyrate, polyhydroxyvaleriate, polycaprolactone, polycaprolactam or a starch.

19. The method of claim 9, wherein said biodegradable polymer is poly $\epsilon$-caprolactone.

20. The method of claim 15, wherein said composite material comprises a matrix of a mixture of water soluble glass fibers and water soluble glass particles impregnated with said biodegradable polymer.

* * * * *